(12) United States Patent
Gellert et al.

(10) Patent No.: US 9,116,160 B2
(45) Date of Patent: Aug. 25, 2015

(54) METHOD AND ARRANGEMENT FOR GAS CHROMATOGRAPHIC ANALYSIS OF A GAS SAMPLE

(75) Inventors: Udo Gellert, Bartlesville (DE); Frank Probst, Herxheim bei Landau/Pfalz (DE)

(73) Assignee: Siemens Aktiengesellschaft, Munich (DE)

( * ) Notice: Subject to any disclaimer, the term of this patent is extended or adjusted under 35 U.S.C. 154(b) by 569 days.

(21) Appl. No.: 13/511,925

(22) PCT Filed: Nov. 25, 2010

(86) PCT No.: PCT/EP2010/068238
§ 371 (c)(1),
(2), (4) Date: Sep. 19, 2012

(87) PCT Pub. No.: WO2011/064310
PCT Pub. Date: Jun. 3, 2011

(65) Prior Publication Data
US 2013/0133403 A1    May 30, 2013

(30) Foreign Application Priority Data

Nov. 25, 2009   (DE) .......................... 10 2009 055 785
Jul. 5, 2010    (DE) .......................... 10 2010 026 078

(51) Int. Cl.
*G01N 30/66* (2006.01)
*G01R 27/26* (2006.01)
*G01N 30/86* (2006.01)
(Continued)

(52) U.S. Cl.
CPC ............ *G01N 30/8631* (2013.01); *G01N 30/04* (2013.01); *G01N 30/66* (2013.01); *G01N 2030/8859* (2013.01); *G01R 27/2629* (2013.01)

(58) Field of Classification Search
CPC ................ G01N 2030/025; G01N 2030/3053; G01N 30/66; G01N 30/68
See application file for complete search history.

(56) References Cited

U.S. PATENT DOCUMENTS 3,480,397 A * 11/1969 Baumgartel .................. 436/137
3,616,677 A * 11/1971 Oppegaard .................... 73/23.21
(Continued)

FOREIGN PATENT DOCUMENTS

| CN | 1508541 | 6/2004 |
|---|---|---|
| CN | 1566944 | 1/2005 |

(Continued)

OTHER PUBLICATIONS

Diaham et al., Electrical Conductivity of Parylene F at High Temperature, Journal of Electronic Materials, 2011, vol. 40, No. 3, pp. 295-300.*

(Continued)

*Primary Examiner* — David A Rogers
(74) *Attorney, Agent, or Firm* — Cozen O'Connor

(57) ABSTRACT

The invention relates to a gas sample to be analyzed, wherein said sample is guided by means of a carrier gas through a separator unit having a downstream thermal conductivity detector providing a chromatogram having peaks for different analytes as a measurement signal. When using a thermal conductivity detector having a heated gold thread coated with a parylene F, hydrogen is used as a carrier gas, and a peak for the analyte hydrogen sulfide is generated by differentiating the chromatogram at the location of said analyte. The invention permits unlimited use of hydrogen as a carrier gas, even if the analyte is oxygen.

6 Claims, 3 Drawing Sheets

(51) Int. Cl.
*G01N 30/04* (2006.01)
*G01N 30/88* (2006.01)

(56) References Cited

U.S. PATENT DOCUMENTS

| | | | |
|---|---|---|---|
| 3,628,003 A | | 12/1971 | Spence et al. |
| 3,634,757 A | * | 1/1972 | Monomakhoff ............ 324/693 |
| 3,683,671 A | * | 8/1972 | Van Swaay ................. 73/25.03 |
| 4,918,974 A | * | 4/1990 | Hachey et al. .............. 73/19.07 |
| 4,987,010 A | | 1/1991 | Krause et al. |
| 5,047,073 A | * | 9/1991 | Stetter et al. ........................ 95/8 |
| 5,081,869 A | * | 1/1992 | Hachey et al. .............. 73/25.03 |
| 5,265,459 A | * | 11/1993 | Cohen ......................... 73/25.03 |
| 5,379,630 A | * | 1/1995 | Lacey ......................... 73/25.03 |
| 5,883,310 A | | 3/1999 | Ho et al. |
| 6,357,279 B1 | * | 3/2002 | Willis ......................... 73/25.03 |
| 6,845,650 B2 | | 1/2005 | Mueller |
| 6,896,406 B2 | | 5/2005 | Gellert |
| 7,670,046 B2 | * | 3/2010 | Mitov ............................. 374/44 |
| 7,791,814 B2 | * | 9/2010 | Liogier D'ardhuy et al. 359/665 |
| 8,310,838 B2 | * | 11/2012 | Kellermann ................. 361/772 |
| 2002/0170904 A1 | * | 11/2002 | Rust .............................. 219/385 |
| 2003/0134426 A1 | * | 7/2003 | Jiang et al. .................... 436/121 |
| 2004/0144169 A1 | | 7/2004 | Popielas et al. |
| 2004/0181155 A1 | * | 9/2004 | Glukhovsky ................. 600/476 |
| 2004/0201926 A1 | * | 10/2004 | Hancer et al. .............. 360/294.4 |
| 2005/0008848 A1 | * | 1/2005 | Saccomanno et al. ........ 428/328 |
| 2006/0101899 A1 | * | 5/2006 | Hastings ...................... 73/23.41 |
| 2006/0144126 A1 | * | 7/2006 | O'Brien et al. .............. 73/23.42 |
| 2007/0209433 A1 | | 9/2007 | Gehman et al. |
| 2009/0141767 A1 | | 6/2009 | Cummins |
| 2009/0167432 A1 | * | 7/2009 | van den Heuvel .............. 330/69 |
| 2009/0192577 A1 | * | 7/2009 | Desai ........................... 607/116 |
| 2011/0107816 A1 | * | 5/2011 | Barth .......................... 73/25.03 |
| 2012/0118722 A1 | * | 5/2012 | Holtzapple et al. ............. 203/11 |

FOREIGN PATENT DOCUMENTS

| | | |
|---|---|---|
| DE | 39 06 405 | 9/1990 |
| DE | 10 2009 01461 | 8/2010 |
| EP | 1178309 A1 * | 2/2002 ............. G01N 30/18 |
| EP | 1 381 854 | 12/2005 |
| JP | 61-226659 | 10/1986 |
| JP | 08320312 A * | 12/1996 ............. G01N 30/66 |
| WO | WO 02/50530 | 6/2002 |
| WO | WO 2007/106689 | 9/2007 |
| WO | WO 2008/098820 | 8/2008 |
| WO | WO 2009/095494 | 8/2009 |

OTHER PUBLICATIONS

James Licari, "Coating Materials for Electronic Applications—Polymers, Processes, Reliability, Testing", William Andrew Publishing, 2003, pp. 1-200.*

Meng et al., "A biocompatible Parylene thermal flow sensing array", Sensors and Actuators, No. 144, Dec. 26, 2007.*

Shuqing et al; "Gas Chromatographic Analysis of Sulfur Recovery Procedure Gas"; Chemical Production and Technology; vol. 8, No. 4; Aug. 25, 2010; pp. 32-34.

Radford-Knoery et al; "Determination of Carbonyl Sulfide and Hydrogen Sulfide Species in Natural Waters Using Specialized Collection Procedures and Gas Chromatography with Flame Photometric Detection"; Analytical Chemistry; vol. 65, No. 8; Apr. 15, 1993; pp. 976-982.

Huaijiang et al; "Determination of Trace Water and Hydrogen Sulfide in Liquid Hydrocarbons by Gas Chromatography"; Petrochemical Technology & Application; vol. 19, No. 2; Apr. 25, 2010; pp. 116-118.

Rath, H. J. et al., "Gas Chromatographic Analysis of traces of Hydrogen Sulfide in Hydrogen", Chromatographic, vol. 13, No. 8, 1980, pp. 513-514.

Farmer, B. et al., "Options in gas chromatographic techniques for measurement of H2S in fuel gas", 54$^{th}$ Analysis Division Symposium 2009, vol. 478, pp. 73-92.

Meng, E. and Y.-C. Tai: "A Parylene MEMS Flow Sensing Array" in Transducers 2003, Boston MA.

* cited by examiner

METHOD AND ARRANGEMENT FOR GAS CHROMATOGRAPHIC ANALYSIS OF A GAS SAMPLE

CROSS-REFERENCE TO RELATED APPLICATIONS

This is a U.S. national stage of application No. PCT/EP2010/068238 filed 25 Nov. 2010. Priority is claimed on German Application Nos. 10 2009 055 785.7 filed 25 Nov. 2009 and 10 2010 026 078.9 filed 5 Jul. 2010, the contents of which are incorporated herein by reference in their entirety.

BACKGROUND OF THE INVENTION

1. Field of the Invention

The invention relates to a method for gas chromatographic analysis of a gas sample, which is conveyed by a carrier gas through a separating device having a downstream thermal conductivity detector, which delivers a chromatogram having peaks for different analytes as a measurement signal.

The invention furthermore relates to a corresponding arrangement for gas chromatographic analysis of a gas sample.

2. Description of the Related Art

In chromatography, a sample of a substance mixture to be analyzed is conveyed by a carrier gas through a chromatographic separating device. Because of different migration rates through the separating device, the analytes i.e., the individual substances of the substance mixture reach the output of the separating device at different times, and are successively detected there by a suitable detector. As its measurement signal, the detector generates a chromatogram that consists of a baseline and a number of peaks corresponding to the separated substances. In practice, the chromatogram is affected by noise, with the individual peaks standing out more or less clearly from the signal noise. With well-resolved peaks, the peak area above the noise-free baseline is proportional to the concentration of the analyte; the peak area, in contrast to the peak height, provides accurate measurement results even for asymmetrical peaks.

In gas chromatography, thermal conductivity detectors are preferably used for detecting the separated analytes with the aid of their substance-typical thermal conductivity. To this end, as described, for example, in EP 1381854 B1, the separated analytes are successively conveyed in a channel past an electrically heated heating filament arranged therein, in which case more or less heat is transferred from the heating filament to the channel wall depending on the thermal conductivity of the analyte flowing past in comparison with that of the carrier gas, and the heating filament is correspondingly cooled or heated to a greater or lesser extent. The electrical resistance of the heating filament therefore changes, and this change in electrical resistance is detected. To this end, the heating filament is conventionally arranged in a measurement bridge that contains another heating filament in a further channel through which a reference gas flows.

The detection sensitivity of the thermal conductivity detector is commensurately greater when the temperature difference between the heating filament and the channel wall is greater, although high temperatures compromise the lifetime of the heating filament. The detection sensitivity also depends on the electrical resistivity of the heating filament, because with a predetermined geometry of the heating filament its total resistance is dictated by this. The greater this total resistance is, the greater is the detection sensitivity. Lastly, chemically aggressive gases may attack and destroy the heating filament.

In the thermal conductivity detector known from EP 1381854 B1, the heating filament consists of gold and/or platinum. At about 15 to 25 Ω, the heating filament resistance achievable with gold is low and limits the detection sensitivity. In order to reach a heating filament resistance typically of 20 Ω, in terms of its dimensions the gold filament must be made very thin (<0.3 μm) and narrow (typically 6 μm) for a length of 1 mm. Such filigree dimensions lead to a very low heat capacity and therefore to a very short response time, but also to poor robustness. Moreover, gases containing hydrogen sulfide can destroy the gold filament. Platinum has a much higher melting temperature than gold and five times its resistivity, with almost the same temperature coefficient of the electrical resistance. The advantage of platinum is its chemical inertness, although this means that production in thin-film technology proves very difficult. Another disadvantage is the catalytic effect of platinum in gas mixtures which contain hydrogen and hydrocarbons.

DE 39 06 405 A1 discloses a thermal conductivity detector for gas analyzers, in which the heating element is not a free-lying heating filament but a resistor layer formed on a support plate. For protection against aggressive gases, the resistor layer is coated with a plasma enhanced chemical vapor deposition (PECVD) layer.

WO 2007/106689 A2, WO 2008/098820 A1 and E. Meng and Y.-C. Tai: "A Parylene MEMS Flow Sensing Array" in Transducers 2003, 2003, Boston, Mass., respectively disclose a thermal mass flow rate sensor in which free-lying heating and/or sensor elements are provided with a protective layer of parylene.

Parylene is a generic term for polymeric coating materials of which, in particular, the parylene types parylene N (poly(para-xylylene)), parylene C (poly(chloro-para-xylylene)), parylene D (poly(dichloro-para-xylylene)) and parylene F (poly(tetrafluoro-para-xylylene)) are industrially employed. Although the melting point of parylene N is very high, at 410° C., the mechanical properties change with an increasing temperature. The thermal stability is the lowest of all the parylene types, particularly in an oxygen environment. Although parylene C has very good barrier properties, i.e., very low gas permeabilities, the melting point at 290° C. is the lowest of the parylene types mentioned here. Parylene D has a relatively high thermal stability of up to 380° C. The mechanical and electrical properties are best preserved under an increase in temperature compared with parylene N and parylene C. At more than 500° C., the melting point of parylene F is far higher than the other three parylene types. Parylene F has the highest melting point, at more than 500° C., compared with the other three parylene types, as well as the highest thermal stability. Parylene F is chemically very similar to parylene N, so that the gas permeability of the two is about the same, i.e., permeable for oxygen and to a very high extent also permeable for hydrogen sulfide.

SUMMARY OF THE INVENTION

It is an object of the invention to provide a method for gas chromatographic analysis of a gas sample using a thermal conductivity detector having a parylene-coated gold filament and taking into account the properties of parylene.

This and other objects and advantages are achieved in accordance with the invention by providing a method in which hydrogen is used as the carrier gas and a thermal conductivity detector having an electrically heated gold filament coated with parylene F and in which a peak for the analyte hydrogen sulfide is generated by differentiating the chromatogram at the position of this analyte.

Prior observations of thermal conductivity detectors having uncoated gold filament have revealed that the heated gold filament becomes conditioned, i.e., modified, on its surface by hydrogen sulfide. As a result, particularly in the case of a very thin and narrow gold filament, its electrical resistance changes. The modification of the gold filament is reversible, and is reversed in an oxygen or hydrogen environment. Thermal conductivity detectors having gold filaments have not previously been used in gas chromatography when hydrogen sulfide was to be detected. The same also applies for the detection of oxygen in the presence of hydrogen as a carrier gas, because the alternate oxidation on the surface of the gold filament by the oxygen and reduction by the hydrogen leads to a drift of the baseline in the chromatogram.

Parylene F is impermeable for most molecules, for example, including for oxygen. For some molecules, such as helium, hydrogen and hydrogen sulfide, however, this parylene is permeable. Breakdown of the hydrogen sulfide-induced conditioning of the heated gold filament is therefore not possible with oxygen, but with hydrogen it is. It has, however, been found that the measurement signal delivered by the thermal conductivity detector, when the analyte hydrogen sulfide occurs, is essentially dependent on the electrical resistance change due to the hydrogen sulfide-induced conditioning of the heated gold filament, and is not influenced or only slightly influenced by the difference between the thermal conductivity of hydrogen sulfide and that of hydrogen. The directly obtained measurement signal for hydrogen sulfide thus forms the integral curve of a peak, for which reason the chromatogram is differentiated at the position of the analyte hydrogen sulfide by forming the first derivative and a peak for this analyte is thereby generated. For the analytes directly following hydrogen sulfide, the baseline of the chromatogram is raised until the hydrogen sulfide-induced conditioning of the gold filament has been broken down again by the hydrogen. The evaluation of the peaks, for example, determination of the peak area, is however performed from the baseline, so that its height does not compromise the measurement.

Lastly, owing to the impermeability of parylene for oxygen, the thermal conductivity detector comprising the parylene-coated gold filament allows unrestricted use of hydrogen as a carrier gas, i.e., even in the case of the analyte oxygen.

In the case of process chromatographs, implementing the differentiation of the chromatogram by appropriate modification of or addition to existing evaluation software entails considerable development outlay in terms of time and cost. In order to minimize this outlay, the measurement signal may advantageously be differentiated by an RC component, which is formed by connecting the thermal conductivity detector by at least one capacitor to an input of an evaluation device.

The invention therefore also relates to an arrangement for gas chromatographic analysis of a gas sample, which is conveyed by a carrier gas through a separating device having a downstream thermal conductivity detector, which delivers a chromatogram having peaks for different analytes as a measurement signal, where hydrogen is used as the carrier gas and a thermal conductivity detector having an electrically heated gold filament coated with parylene F, where a peak for the analyte hydrogen sulfide is generated by differentiating the chromatogram at the position of this analyte, and where the thermal conductivity detector is connected by at least one capacitor to an input of an evaluation device to produce an RC component that differentiates the measurement signal.

In the case of an evaluation device comprising at least two inputs, the measurement signal is delivered differentiated to one input and unmodified to the other input.

The hardware implementation of the differentiation of the chromatogram makes do with only a capacitor, or respectively one capacitor for each of the two input branches, and therefore involves extremely little outlay.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention, reference will be made below to the figures of the drawing in which.

DETAILED DESCRIPTION OF THE PREFERRED EMBODIMENTS

Figure 1:
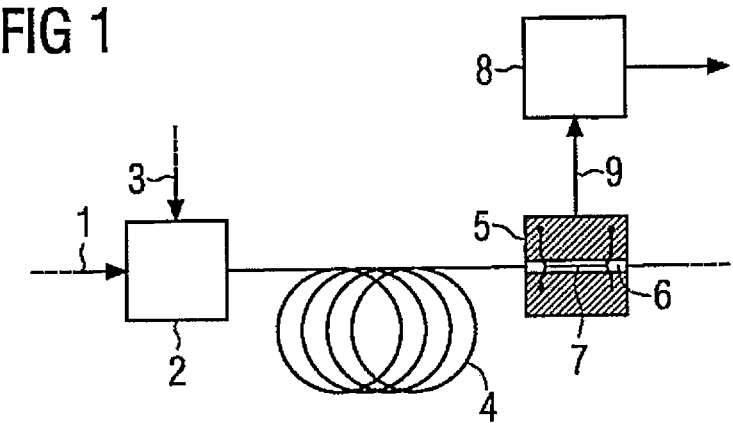
FIG. 1 shows a simplified schematic block diagram of an exemplary gas chromatograph in accordance with the invention.

FIG. 1 shows a chromatograph in which hydrogen as a carrier gas 1 is delivered to an injector 2, loaded there with a sample 3 of a substance mixture to be analyzed, and subsequently introduced into a separating device 4 as a separating capillary or circuit of separating capillaries. The separated sample components (analytes) emerging successively from the separating device 4 travel to a thermal conductivity detector 5. There, the separated analytes are conveyed in a channel 6 past an electrically heated heating filament 7 arranged therein, which consists of gold and, like the channel wall, is coated with parylene F. Depending on the thermal conductivity of the analyte respectively flowing past in comparison with that of the carrier gas, more or less heat is transferred from the heating filament 7 to the channel wall so that the heating filament 7 is correspondingly cooled or heated. As a result, the electrical resistance of the heating filament 7 changes, and this change in electrical resistance is detected in an evaluation device 8. To this end, the heating filament is conventionally arranged in a measurement bridge (not shown) that contains another heating filament in a further channel through which a reference gas, for example, the carrier gas 1, flows.

Figure 2:
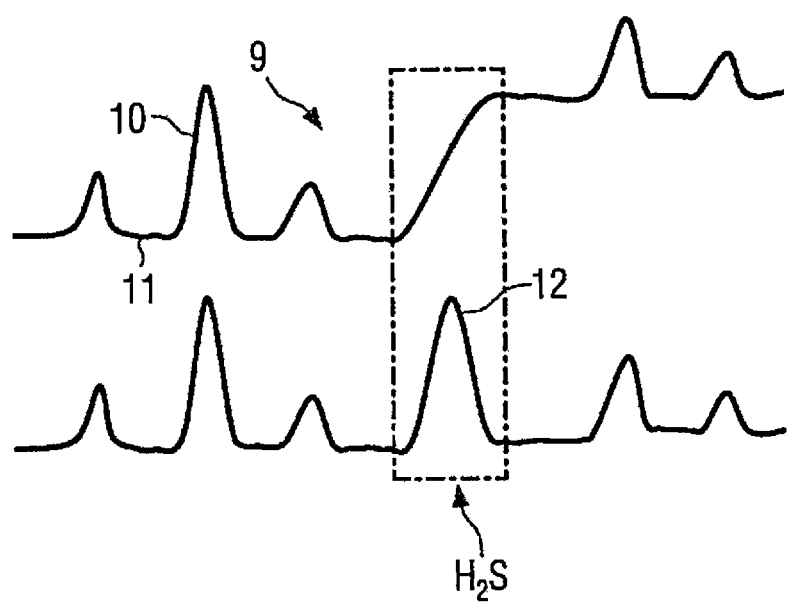
FIG. 2 shows an exemplary graphical plot of an acquired chromatogram and the processed chromatogram.

As its measurement signal 9, the thermal conductivity detector 5 delivers a chromatogram, shown in a very simplified representation in the upper part of FIG. 2, comprising peaks for different analytes. The chromatogram 9 is digitally evaluated in the evaluation device 8 such that the peaks, such as 10, due to the different analytes are identified in the signal noise usually present and their area above the baseline 11, corresponding to the concentration of the analyte, is determined.

Parylene F is permeable for hydrogen sulfide ($H_2S$). Consequently, the heated gold filament 7 of the thermal conductivity detector 5 becomes conditioned when this analyte occurs, such that its electrical resistance increases. This effect is so great that it masks the thermal conductivity measurement per se. The conditioning of the gold filament 7 is subsequently broken down again by the carrier gas hydrogen. The chromatogram 9 therefore has a step-like profile at the position of the analyte hydrogen sulfide, the step height being dependent on the concentration of hydrogen sulfide.

As can be seen in the lower part of FIG. 2, the chromatogram 9 is differentiated in the region of the analyte hydrogen sulfide by forming the first derivative and a peak 12 for this analyte is thereby generated. This region is selected to be large enough that a baseline 11' sufficient for the evaluation of the peak 12 is generated before and after the peak 12. For the analytes directly following hydrogen sulfide, the baseline 11 of the chromatogram 9 is raised (offset) until the hydrogen sulfide-induced conditioning of the gold filament 7 has been broken down again by the hydrogen. The evaluation of the peaks, for example, determination of the peak area, is however performed from the baseline 11, so that its height does not compromise the measurement. In the lower part of FIG. 2, the offset of the baseline 11 is calculated out of the chromatogram 9, i.e., the peaks following the peak 12 generated by differentiation are pulled down to the baseline level 11' of the peak 12.

Figure 3:
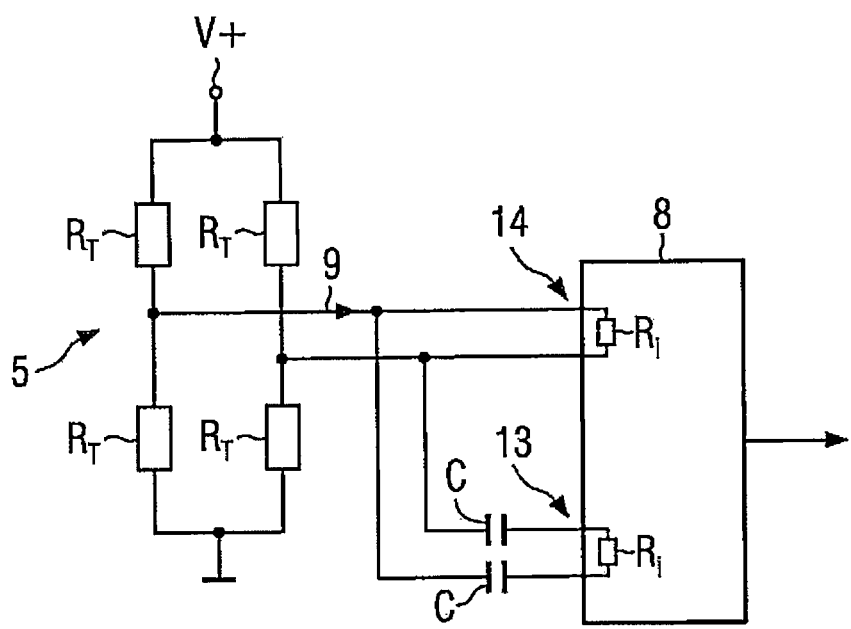
FIG. 3 shows an exemplary hardware implementation of the differentiation of the chromatogram in accordance with the invention.

FIG. 3 shows a circuit diagram of the thermal conductivity detector 5, comprising four resistors $R_T$ which are arranged in a bridge circuit. Each resistor $R_T$ corresponds to a gold filament 7 (FIG. 1), with the chromatographically separated sample 3 flowing around two gold filaments 7 lying diagonally opposite in the bridge circuit and with the carrier gas 1 flowing around the other two gold filaments 7. The evaluation device 8 has two or more channels, and accordingly comprises at least two analog inputs 13 and 14. The measurement signal 9 of the thermal conductivity detector 5 is delivered unmodified to the input 14 and differentiated to the input 13. To this end, a capacitor C is respectively inserted into each of the two input branches of the input 13, which capacitor forms a differentiating RC component with the input resistor $R_i$.

With $f_u$ being the lowest frequency and $f_o$ being the highest frequency in the measurement signal profile considered, C is then given in the bandwidth between:

$$1/[2\pi f_o \cdot (R_i+R_T)] < C < 1/[2\pi f_u \cdot (R_i+R_T)],$$

i.e., for example, 32 µF<C<160 µF for $f_u$=0.1 Hz, $f_o$=5 Hz and $R_i+R_T \approx 1000\ \Omega$.

Figure 4:
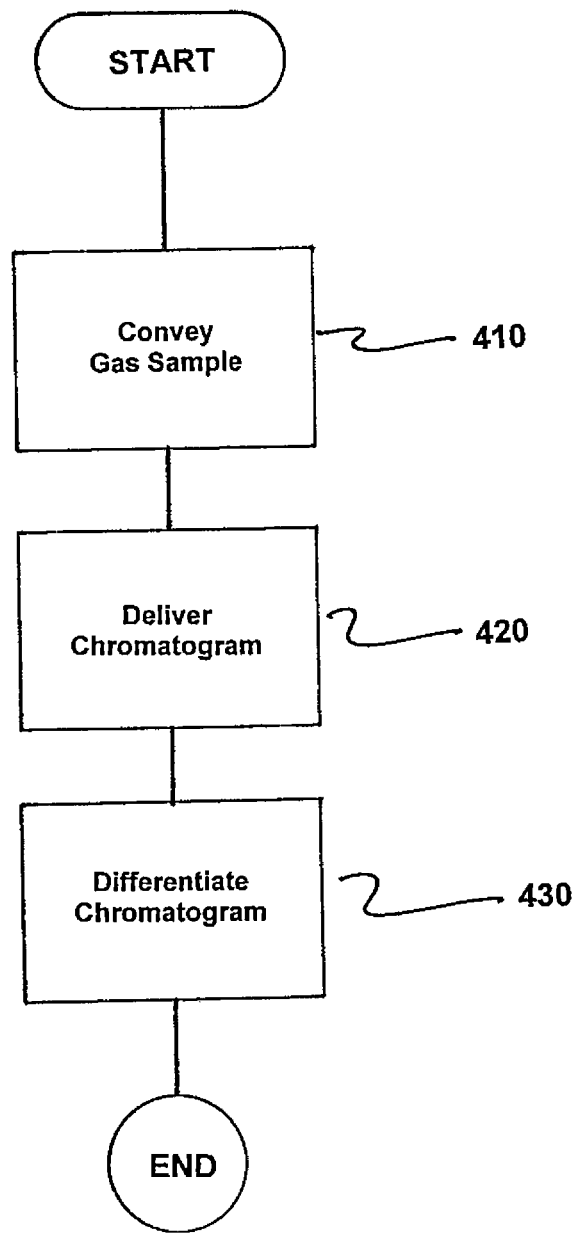
FIG. 4 is a flow chart of the method in accordance with the invention.

FIG. 4 is a flow chart of a method for gas chromatographic analysis of a gas sample. The method comprises conveying the gas sample by a carrier gas comprising hydrogen through a separating device having a downstream thermal conductivity detector including an electrically heated gold filament coated with parylene F, as indicated in step 410.

A chromatogram having peaks for different analytes is delivered as a measurement signal from the thermal conductivity detector, as indicated in step 420.

The chromatogram is differentiated at a position of an analyte of the different analytes to generate a peak for a hydrogen sulfide analyte, as indicated in step 430.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for gas chromatographic analysis of a gas sample, comprising:
   conveying the gas sample by a carrier gas comprising hydrogen through a separating device having a downstream thermal conductivity detector including an electrically heated gold filament coated with parylene F;
   delivering, from the thermal conductivity detector, a chromatogram having peaks for different analytes as a measurement signal; and
   differentiating the chromatogram at a position of an analyte of the different analytes to generate a peak for a hydrogen sulfide analyte.

2. The method as claimed in claim 1, wherein an oxygen analyte is detected in the carrier gas hydrogen.

3. The method as claimed in claim 1, wherein the measurement signal is differentiated by an RC component formed by connecting the thermal conductivity detector by at least one capacitor to an input of an evaluation device.

4. The method as claimed in claim 3, wherein an oxygen analyte is detected in the carrier gas hydrogen.

5. An arrangement for gas chromatographic analysis of a gas sample, comprising:
   a separating device having a downstream thermal conductivity detector including an electrically heated gold filament coated with parylene F, the gas sample being conveyed by a carrier gas through the separating device, the thermal conductivity detector delivering a chromatogram having peaks for different analytes as a measurement signal, and a carrier gas comprising hydrogen being conveyed through the thermal conductivity detector;
   an evaluation device having an input; and
   at least one capacitor connecting the thermal conductivity detector to the input of the evaluation device to produce an RC component which differentiates the measurement signal, the chromatogram being differentiated by the evaluation unit at a position of an analyte of the different analytes to generate a peak for a hydrogen sulfide analyte.

6. The arrangement as claimed in claim 5, wherein the evaluation device comprises at least two inputs, one of the inputs receives the measurement signal differentiated by the RC component and the other of the inputs receives the measurement signal unmodified.

* * * * *